(12) United States Patent
Stuttard

(10) Patent No.: US 6,753,967 B2
(45) Date of Patent: Jun. 22, 2004

(54) GAS SENSOR

(75) Inventor: David Michael Stuttard, Nottinghamshire (GB)

(73) Assignee: Dynament Limited, Nottingham (GB)

( * ) Notice: Subject to any disclaimer, the term of this patent is extended or adjusted under 35 U.S.C. 154(b) by 75 days.

(21) Appl. No.: 09/783,711

(22) Filed: Feb. 14, 2001

(65) Prior Publication Data

US 2002/0105650 A1 Aug. 8, 2002

(30) Foreign Application Priority Data

Feb. 8, 2001 (GB) ............................................. 0103089

(51) Int. Cl.⁷ ............................................. G01N 21/00
(52) U.S. Cl. ..................... 356/437; 356/439; 356/440; 250/343
(58) Field of Search ................................. 356/246, 432, 356/436, 437, 439, 440; 250/343, 353, 574; 73/31.02

(56) References Cited

U.S. PATENT DOCUMENTS

| | | | | |
|---|---|---|---|---|
| 4,190,363 A | * | 2/1980 | Adrian | 356/246 |
| 4,445,359 A | * | 5/1984 | Smith | 356/437 X |
| 4,560,875 A | * | 12/1985 | Crowder | 250/343 |
| 4,700,079 A | * | 10/1987 | Ito | 250/574 |
| 4,810,096 A | * | 3/1989 | Russell et al. | 356/436 |
| 5,060,508 A | * | 10/1991 | Wong | 73/31.02 |
| 5,103,096 A | * | 4/1992 | Wong | 250/343 |
| 5,222,389 A | * | 6/1993 | Wong | 73/31.02 |
| 5,225,786 A | * | 7/1993 | Vaughn et al. | 324/706 |
| 5,340,986 A | * | 8/1994 | Wong | 250/343 |
| 5,341,214 A | * | 8/1994 | Wong | 356/437 |
| 5,488,227 A | * | 1/1996 | Sweet | 250/343 |
| 5,517,314 A | * | 5/1996 | Wallin | 356/437 |
| 5,834,777 A | * | 11/1998 | Wong | 250/343 |
| 5,925,881 A | * | 7/1999 | Wahlbrink | 250/343 |
| 5,973,326 A | | 10/1999 | Parry et al. | 250/343 |
| 6,157,455 A | * | 12/2000 | Pinvidic et al. | 356/437 |
| 6,326,897 B2 | * | 12/2001 | Kadwell et al. | 250/574 X |
| 6,469,303 B1 | * | 10/2002 | Sun et al. | 250/343 |
| 2002/0063216 A1 | * | 5/2002 | Clausen et al. | 250/343 |

FOREIGN PATENT DOCUMENTS

| | | | |
|---|---|---|---|
| GB | 2246877 | | 2/1992 |
| GB | 2 261 502 A | * | 5/1993 |
| GB | 2301665 | | 12/1996 |
| GB | 2316172 | | 2/1998 |
| GB | 2358245 | | 7/2001 |
| JP | 4-104040 A | * | 4/1992 |

OTHER PUBLICATIONS

AMG Optical Gas Detection web page; 1995 (No month available).
EEV Infra Red Data Sheet; 1997 (No month available).
Simrad Optronics Data Sheet; 1994 (No month available).
AMG Optical Gas Detection web page, No date available.
EEV data sheet, Subsidy of General Electric Company, England, No date available.

* cited by examiner

Primary Examiner—Jared J. Fureman
(74) Attorney, Agent, or Firm—Ryan Kromholz & Manion, S.C.

(57) ABSTRACT

A gas sensor of the type that detects the presence of a specific gas by monitoring the absorption of optical radiation transmitted through a chamber containing a sample of gas under test comprises an optical source for emmiting radiation therefrom and a detector sensitive to radiation emitted from the source at opposing ends of a circumferential chamber, having optically reflective surfaces, extending around the periphery of a sensor housing The optical pathway between the source and detector may include a radial portion as well as a circumferential portion to allow one or other of the source and detector to be located in a central chamber of the sensor housing.

25 Claims, 2 Drawing Sheets

GAS SENSOR

FIELD OF THE INVENTION

The present invention relates to gas sensors, and in particular to gas sensing devices that detect the presence of a specific gas by monitoring the absorption of optical radiation transmitted through a chamber containing a sample of gas under test.

BACKGROUND OF THE INVENTION

Gas sensors utilising an infra-red source and a corresponding infra-red detector are well known, in particular in the design of, for example, carbon dioxide and hydrocarbon gas detectors. Infra-red radiation emitted by the source is focussed onto the detector, having passed through a chamber containing the gas under test, where some of the infra-red radiation will be absorbed by the gas. The absorption by a specific gas is a function of the wavelength of the infra-red radiation, and by careful selection of an appropriate optical band-pass filter at the detector, it is possible to determine the presence of a specific gas.

A particularly important aspect of the design of optical absorption gas sensors is the path length between source and detector. In many known systems, long path lengths are used to increase the degree of absorption observed, typically by mounting the infra-red source and detector in separate housings for remote location from one another using long tubes or free space therebetween to define the optical path between source and detector. Such systems typically require pumping of gas through the detection chamber.

There is, however, a commercial requirement for highly compact, integral sensors, that can be simply plugged into, for example, portable gas detection units. This severely compromises the absorption path length available. In one compact sensor, as described in GB 2316172, a design of sensor attempts to increase path length between source and detector in a common housing and maximise signal to noise ratio characteristics by arranging the source and sensor at respective foci of an ellipsoidal chamber in which the light traveling between source and sensor is reflected at least three times. The sensor described requires high quality, polished focussing curved surfaces and careful positioning of the source and sensor elements.

SUMMARY OF THE INVENTION

The present invention aims to provide a highly compact gas sensor that is easy and cost effective to manufacture and assemble that avoids the need for focussing surfaces and careful positioning of source or detector elements.

According to one aspect, the present invention provides a gas sensor comprising:
an optical source for emitting radiation therefrom;
a detector sensitive to radiation emitted from the source;
a circumferential chamber, having optically reflective surfaces, extending between the source and the detector.

According to another aspect, the present invention provides a gas sensor comprising:
an optical source for emitting radiation therefrom;
a detector sensitive to radiation emitted from the source;
a chamber, extending between the source and the detector, defined by a plurality of non-focussing, planar surfaces disposed to form a folded optical pathway that includes a plurality of segments substantially parallel to one another.

BRIEF DESCRIPTION OF THE DRAWINGS

Embodiments of the present invention will now be described by way of example and with reference to the accompanying drawings in which.

DETAILED DESCRIPTION OF THE INVENTION

Figure 1:
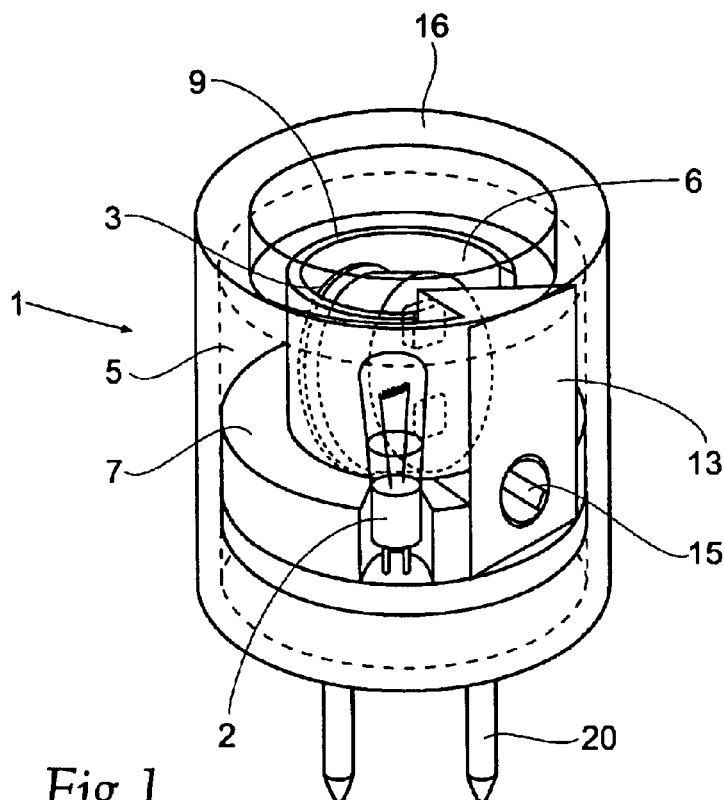
FIG. 1 is a schematic perspective view of a sensor according to one embodiment of the present invention showing internal detail.

Throughout the present specification, expressions of relative position such as "top", "bottom", "cap", "base", "up", "down" etc, are used solely for convenience and clarity in relation to the sensor as oriented in the drawings. They are in no way intended to be limiting as to the orientation of use of the sensors described.

With reference to the figures, a gas sensor 1 comprises an optical source 2 for emitting radiation in the optical spectrum. The expression "optical" is intended to cover all parts of the electromagnetic spectrum that are useful for the function of gas detection by absorption and includes the infra-red, visible, and ultra-violet ranges of the electromagnetic spectrum. The source is preferably of the incandescent variety, producing a broad range of frequencies with which to measure absorption characteristics, but may also be of the solid state variety such as diodes producing limited frequencies or frequency bands.

The gas sensor 1 further comprises a detector 3 for detection of radiation emitted by the source 2. The detector 3 may be of any suitable type for sensing variations in intensity of radiation received from the source and providing as output a voltage or current as a function thereof. In a preferred embodiment, operating in the infra-red spectrum, the detector 3 is a pyroclectric detector.

Figure 2:
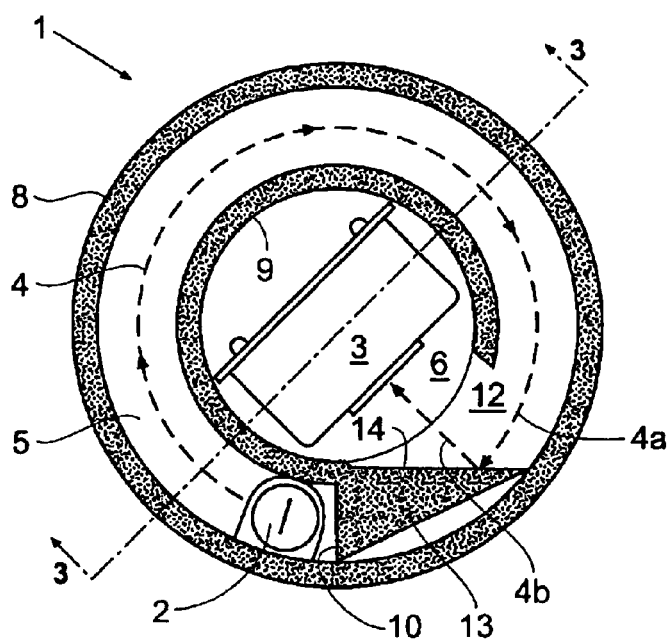
FIG. 2 is a plan view of the sensor of FIG. 1, with the top cover removed.

The source 2 and detector 3 arc respectively located at opposite ends of an optical pathway 4 (FIG. 2) which pathway is defined by a circumferential chamber 5 and a central chamber 6 respectively defining a generally circumferential portion 4a of the optical pathway 4 and a generally radial portion 4b of the optical pathway.

Figure 3:
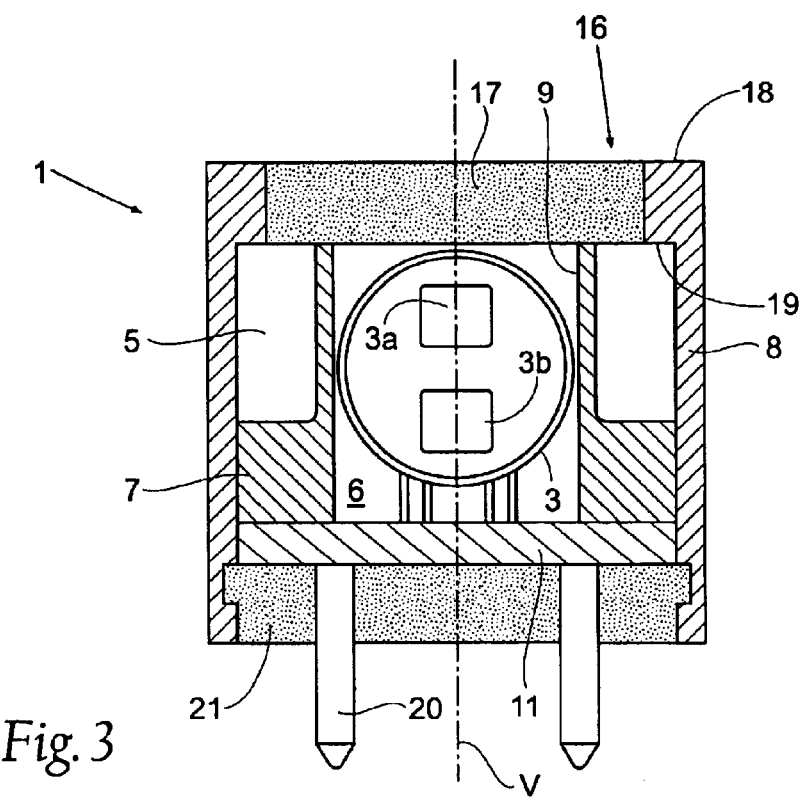
FIG. 3 is a cross-sectional side view taken on line 3–3 of FIG. 2.

As best seen in FIG. 3, the circumferential chamber 5 is defined by: a chamber base 7; an internal surface of an outer cylindrical wall 8 of the sensor housing; an external surface of an inner cylindrical wall 9 of the sensor housing; and a radial end wall 10. Preferably, the chamber base 7 provides a planar reflective surface, although a non-planar surface could be used. Although in the preferred embodiment the walls of the circumferential chamber 5 are formed from cylindrical walls 8, 9, it will be understood that some departure from smooth convex and concave surfaces is possible, for example using a multifaceted configuration to form generally circumferential walls. The circumferential walls could also be concave or convex along the axial direction. The radial end wall 10 is preferably planar, but could also be non-planar.

The central chamber 6 is defined by an internal surface of the housing base 11 and an internal surface of the inner cylindrical wall 9 of the sensor housing. Preferably, the housing base 11 provides a planar reflective surface, in the central chamber 6, although non-planar surfaces could be used. Although, in the preferred embodiment, the curved wall of the central chamber 6 is formed from the inner cylindrical wall 9, it will he understood that some departure from a smooth concave surface is possible, for example using a multifaceted configuration to form the internal surface. The internal surface could also be concave or convex along the axial direction.

Optical communication between the circumferential chamber 5 and the central chamber 6 is by way of a gap 12 in the inner cylindrical wall 9. To enhance reflection of radiation from the circumferential chamber 5 to the central chamber 6, a deflector element 13 provides a reflecting surface 14 which generally extends from the outer cylindrical wall 8 to the inner cylindrical wall 9. The reflecting surface 14 is preferably planar but may also be non-planar. The reflecting surface 14 is generally oblique to the tangent of the outer and inner circumferential walls 8, 9 at the position of the gap, but may also be radial.

The deflector 13 is preferably formed from a wedge shaped element which also forms the radial end wall 10. The wedge shaped element can be fixed into position by screw 15 which may allow for some adjustment in the angle of the wedge shaped element. Alternatively, a reflector, fabricated from sheet metal and located in position by a pin or spot welding, may be used.

The top 16 of the sensor housing includes a gas permeable window 17 to allow controlled diffusion of gas under test from the external ambient of the sensor housing to the optical pathway 4 in the chambers 5 and 6. Preferably, the gas permeable window 17 comprises a disc shaped element of sintered flame arresting material that allows diffusion of gas but forms a combustion barrier so that the source 2 cannot accidentally act as an ignition source when the sensor is operating in a hazardous and combustible gaseous environment.

Preferably, the disc element 17 has a radius that is greater than the radius of the inner cylindrical wall 9 and less than the radius of the outer cylindrical wall 8 so that the gas permeable window completely extends over the central chamber 6 and partially extends over the circumferential chamber 5. The remaining portion 18 of the top 16 of the sensor housing provides a reflective inner surface 19 partially covering the circumferential chamber 5 to enhance the optical transmission characteristics of the circumferential chamber.

The detector 3 is mounted in the base 11 of the sensor housing and preferably comprises a dual element pyroelectric detector. The detector elements 3a, 3b are preferably arranged in a spaced relationship along a vertical axis V of the sensor housing, i.e. an axis parallel to the central axis defined by the inner and outer cylindrical walls 8, 9. This axial spacing of the detector elements 3a, 3b ensures that the characteristics of the optical pathways leading to each of the elements are substantially similar. Each element 3a, 3b includes a filter (not shown) to allow the transmission of optical radiation at selected frequencies or frequency ranges. This dual element configuration enables the sensor to operate with one reference or compensation detector to increase accuracy of the measurements, as will be described hereinafter.

Electrical leads 20 to both the source 2 and the sensor 3 pass through the housing base 11 and through an encapsulant layer 21 that holds the base 11 in position. The encapsulant layer 21 also seals the housing so that it is gas tight except for the controlled diffusion window 17.

The housing of sensor 3 may be made to conform to an industry standard configuration in terms of external dimensions and positioning of a plurality of electrical leads 20, not all of which are shown in the drawings. Preferably, the overall outside casing diameter is approximately 2 cm, and the casing height is approximately 2 cm. Preferably, the diffusion window 17 and encapsulant layer 21 each have a minimum thickness of 3 mm to meet safety regulations and are formed from injection moulded or machined plastics material, or metallic parts, as required.

In use of the preferred embodiment, the incandescent source 2 emits infra-red radiation over a broad spectrum of frequencies. The reflective surfaces formed by the inner and outer cylindrical walls 8, 9 and the radial end wall 10 guide the infra red radiation around the circumferential chamber 5. The non-focussing nature of the reflector surfaces means that positioning of the source 2 within the circumferential chamber 5 is not critical. Once the radiation reaches the other end of the circumferential chamber 5, via optical pathway 4a, radiation is reflected off the reflecting surface 14 of deflector 13 onto the radial inward optical path 4b, towards the detector elements 3a, 3b.

The preferred planar geometry of the reflecting surface 14 is such that the radiation incident upon the detector elements 3a, 3b is principally normal to the elements' surfaces which provides optimum temperature characteristics for the sensor 1 and ensures that a substantially equal amount of radiation falls on both elements. This provides for better matching conditions between the two detector element outputs.

The circumferential optical path 4a also utilises the space within the sensor housing in a highly efficient manner, and allows the chamber walls 8, 9 to be formed from cylindrical elements that are easy to manufacture and also easy to assemble. The completion of the optical path 4 with the radial portion 4b enables easy positioning of the detector within a large central chamber 6.

A first detector element, eg. 3a, incorporates an optical filter (not shown) that allows past only radiation in a bandwidth associated with the absorption spectra of the selected gas for detection, eg. carbon monoxide. The second detector element incorporates an optical filter that allows a broader spread of frequencies, or preferably a selected bandwidth different from that of the first filter and relatively immune from undesirable attenuation from other common gases, to provide a reference signal. The reference signal is used to provide compensation of the attenuation measured by the first sensor that arises from temperature, humidity, degradation of the source intensity and other obscuration factors, rather than from the presence of the selected gas in the optical pathway 4. The ratio of the reference and selected gas signals will therefore be substantially unaffected by these other factors.

The gas permeable window 17 ensures that any changes in gas concentrations external to the sensor housing are rapidly communicated to the optical pathway 4 particularly in the circumferential chamber 5, to be sensed by the detector elements 3a, 3b, providing good real time output of sensed gas conditions. The preferred design of gas permeable window 17 as shown ensures that natural diffusion of gas into the circumferential chamber 5 is sufficient so that no pumping of gas through the chamber is required.

A number of variations to the embodiments described above are possible.

For example, although the preferred embodiment provides the source 2 located at the closed end of the circumferential chamber 5, and the detector 3 located in the central chamber 6, it will be understood that these positions may be reversed. Although the preferred embodiment provides a detector 3 in the central chamber 6, the detector could alternatively be located at the end of the circumferential chamber, ie. in the place of the reflecting surface 14, leaving the central chamber free for signal processing components or the like.

In another arrangement, both source and sensor might be located within a divided central portion of the sensor housing, there being a second gap in the inner cylindrical wall to allow radiation from the source to radiate outward and be reflected onto one end of the circumferential path as well as the first gap 12 to allow the radiation to be reflected inward to the detector 3 at the other end of the circumferential portion 4a of the optical path. In this embodiment, deflector element 13 may he appropriately shaped and positioned to provide two opposing oblique reflecting surfaces.

The circumferential chamber 5 need not be circular. For example, a square or generally rectangular package could incorporate a circumferential chamber extending around the four sides of the rectangle. Similarly, a polygonal package, eg. hexagonal, could include a circumferential chamber extending around the sides of the hexagon. The circumferential chamber may also be of a spiral configuration, in which the chamber wraps over itself after one complete circuit of the periphery of the chamber.

Figure 4:
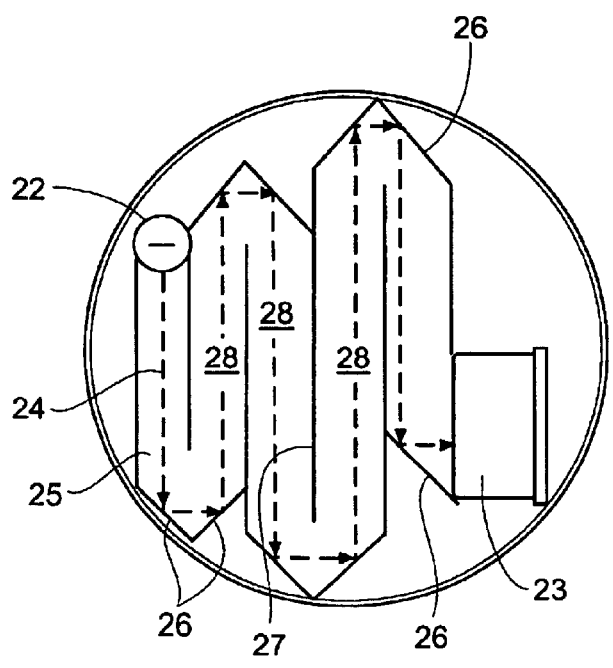
FIG. 4 is a schematic plan view of a sensor having a folded optical path, with the top cover removed.

With reference to FIG. 4, an alternative configuration of detector uses a folded chamber that provides an optical pathway in the form of a snake. In this embodiment, a source 22 is located at one end of a folded chamber 25 providing an optical pathway 24 extending to a detector 23. Multiple reflections along the chamber 25 are provided by angled mirrors 26. Preferably, the chamber walls 27 are also polished mirror surfaces to maximise light transmission through the chamber. In this arrangement, the folded chamber 25 generally includes a plurality of non-focussing, planar surfaces that are disposed to form a folded optical pathway that includes a plurality of segments 28 substantially parallel to one another.

In all of the above described embodiments, some or all of the reflective surfaces may be gold coated (or coated with other suitable reflective material) to enhance signal amplitude, and/or coated with a passivation layer to provide protection against corrosive gases.

The gas permeable window 17 could also be formed from other materials, such as a gauze screen. The gas permeable window 17 need not be disc shaped, but could comprise a series of discrete openings in the top of the housing or be annular in shape.

The detector 3 need not be of the dual element type if a reference detector is not required. Multiple detector elements, each with an appropriate filter, may be provided for simultaneous detection of more than one selected gas.

What is claimed is:

1. A gas sensor comprising:
   an optical source for emitting radiation therefrom;
   a detector sensitive to radiation emitted from the source;
   an optical pathway extending between the source and the detector;
   a chamber having optically reflective surfaces defining a substantially circular portion of the optical pathway and a substantially radial portion of the optical pathway; and
   at least one reflector oriented generally at an oblique angle to the substantially circular portion of the optical pathway to separate the substantially circular portion of the optical pathway and the substantially radial portion of the optical pathway.

2. The gas sensor of claim 1 in which the chamber is defined by outer and inner circumferential walls of a substantially cylindrical housing.

3. The gas sensor of claim 2 further including a first end wall, extending radially between the outer and inner circumferential walls to define a first end of the chamber.

4. The gas sensor of claim 3 further including a second end wall, extending generally radially between the outer and inner circumferential walls and at an oblique angle to a tangent of the outer or inner circumferential walls, to form the at least one reflector to reflect light through a gap in the inner circumferential wall into a central chamber.

5. The gas censor of claim 4 in which the central chamber is defined by an internal surface of the inner circumferential wall.

6. The gas sensor of claim 4 or claim 5 in which the detector is located within the central chamber.

7. The gas sensor of claim 4 or claim 5 in which the source is located within the central chamber.

8. The gas sensor of claim 4 in which the detector is located within the central chamber and comprises two detector elements spaced apart along an axis substantially parallel to the central axis of the circumferential walls.

9. The gas sensor of claim 3 in which the source is located adjacent said first end wall.

10. The gas sensor of claim 3 in which the detector is located adjacent said first end wall.

11. The gas sensor of claim 2 further comprising a chamber cover, forming a closure for the cylindrical housing, the chamber cover including a reflective inner surface in combination with a gas permeable member.

12. The gas sensor of claim 11 in which the gas permeable member comprises a flame arresting material.

13. The gas sensor of claim 11 or claim 12 in which the gas permeable member covers an annular portion of the circumferential chamber.

14. The gas sensor of claim 13 in which the gas permeable member comprises a disc having a radius greater than a radius of said inner circumferential wall and less than a radius of said outer circumferential wall.

15. The gas sensor of claim 1 wherein the optical source emits infra red radiation.

16. The gas sensor of claim 1 wherein the detector senses infra red radiation.

17. The gas sensor of claim 1 wherein the detector is a pyroelectric detector.

18. A method of forming a gas sensor comprising the steps of:
   providing an optical source for emitting radiation therefrom,
   providing a detector sensitive to radiation emitted from the source,
   providing an optical pathway extending between the source and the detector,
   providing a chamber having optically reflective surfaces defining a substantially circular portion of the optical pathway and a substantially radial portion of the optical pathway; and
   providing at least one reflector oriented generally at an oblique angle to the substantially circular portion of the optical pathway to separate the substantially circular portion of the optical pathway and the substantially radial portion of the optical pathway.

19. A gas sensor comprising an optical source for emitting radiation therefrom;

a detector sensitive to radiation emitted from the source; and a circumferential chamber having optically reflective surfaces and extending between the source and the detector, the chamber being defined by outer and inner circumferential walls of a substantially cylindrical housing, the chamber including a first end wall, extending radially between the outer and inner circumferential walls to define a first end of the chamber, and a second end wall, generally radially between the outer and inner circumferential walls and at an oblique angle to a tangent of the outer or inner circumferential walls, to reflect light through a gap in the inner circumferential wall into a central chamber, thereby forming an optical pathway between the source and detector thereby comprising a substantially circumferential portion and a radial portion.

20. The gas censor of claim 19 in which the central chamber is defined by an internal surface of the inner circumferential wall.

21. The gas sensor of claim 19 or claim 20 in which the detector is located within the central chamber.

22. The gas sensor of claim 19 or claim 20 in which the source is located within the central chamber.

23. The gas sensor of claim 19 in which the detector is located within the central chamber and comprises two detector elements spaced apart along an axis substantially parallel to the central axis of the circumferential walls.

24. A gas sensor comprising:

an optical source for emitting radiation therefrom;

a detector sensitive to radiation emitted from the source;

a circumferential chamber having optically reflective surfaces and extending between the source and the detector, the chamber being defined by outer and inner circumferential walls of a substantially cylindrical housing; and a chamber cover forming a closure for the cylindrical housing, the chamber cover including a reflective inner surface in combination with a gas permeable member, the gas permeable member covering an annular portion of the circumferential chamber and comprising a disc having a radius greater than a radius of said inner circumferential wall and less than a radius of said outer circumferential wall.

25. The gas sensor of claim 24 in which the gas permeable member comprises a flame arresting material.

* * * * *